United States Patent
Madugula et al.

(10) Patent No.: US 7,692,016 B2
(45) Date of Patent: Apr. 6, 2010

(54) PROCESS FOR THE SYNTHESIS OF QUINOLINE DERIVATIVES

(75) Inventors: Sree Rama Murty Madugula, Hyderabad (IN); Swamy Thallapelly, Hyderabad (IN); Jyothirmai Bandarupally, Hyderabad (IN); Jhillu Singh Yadav, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 980 days.

(21) Appl. No.: 11/368,279

(22) Filed: Mar. 3, 2006

(65) Prior Publication Data

US 2007/0123708 A1    May 31, 2007

(30) Foreign Application Priority Data

Nov. 25, 2005   (IN)   ........................ 3159/DEL/2005

(51) Int. Cl.
*C07D 215/00*   (2006.01)
(52) U.S. Cl. ...................................... 546/152
(58) Field of Classification Search ................. 546/152
See application file for complete search history.

(56) References Cited

OTHER PUBLICATIONS

Khadilkar et al. Tetrahedron Letters, 38 (9), 1641-, 1997.*
Y. Morimoto, F. Matsuda, H. Shirahama, Synlett, 1991,202.
M. Isobe, T. Nishikawa, N. Yamamoto, T. Tsukiyama, A. Ino, T. Okita, J. Heterocycl. Chem. 1992, 29, 619.
J.P. Michael, Nat. Prod. Rep. 1997, 14, 605.
D.G. Markees, V.C. Dewey, G.W. Kidder, J. Med. Chem. 1970, 13, 324.
J. F. DeBernardis, D.J. Kerkman, J. Med. Chem. 1985, 28, 1398.
S.F. Campbell, J.D. Hardstone, M.J. Palmer, J. Med. Chem. 1988, 31, 1031.
H.V. Patel, K.V. Vyas, P.S. Fernandes; Indian J. Chem. 1990, 29B, 836.
H. Skraup, Chem. Ber. 1880, 13, 2086; R.H.F. Mansake, M. Kulka, Org.React. 1953,7,59.
S.E. Diamond, A. Szalkiewicz, F. Mares, J. Am. Chem. Soc. 1979,101, 490.
T. Joh, N. Hagihara, Tetrahedron Lett. 1967, 8, 4199.
Y.Watanabe, S.C.Shim, T. Mitsudo, Bull. Chem. Soc. Jpn. 1981, 54, 3460.
K.N. Campbell, I. J. Scchaffner, J.A.C.S., 1995, 67, 86-89.
M. A. Clapp, R.S.Yipson, J.A.C.S., 1946, 68, 1332-34.
J.Spencer, M. Pfeffer, Tetrahedron Asymmetry, 1995, 6 (2), 419-426.

* cited by examiner

*Primary Examiner*—D. Margaret Seaman
*Assistant Examiner*—Nizal S Chandrakumar
(74) *Attorney, Agent, or Firm*—Reed Smith LLP; Nanda P. B. A. Kumar

(57) ABSTRACT

The present invention provides an improved process for the synthesis of quinoline derivatives. More particularly the present invention provides an improved and economical process for the synthesis of quinoline derivatives by the reaction of aniline/substituted anilines using two different catalysts, ferric chloride and zinc chloride in a one-pot set up reaction.

11 Claims, No Drawings

PROCESS FOR THE SYNTHESIS OF QUINOLINE DERIVATIVES

This application claims the right of priority under 35 U.S.C. §119(a)-(d) to Indian Patent Application No. 3159/DEL/2005, filed Nov. 25, 2005.

FIELD OF THE INVENTION

The present invention relates to an improved process for the synthesis of quinoline derivatives. More particularly the present invention relates to an improved process for the synthesis of quinoline derivatives by the reaction of aniline/substituted anilines in a one-pot procedure using twin catalysts. Thus the process makes use of two catalysts, first one is a ferric chloride supported on silica (silferc) catalyst and second catalyst is zinc chloride.

BACKGROUND OF THE INVENTION

Quinolines and their derivatives are an important class of compounds in medicinal applications and are widely occurred in natural products [(a) Y. Morimoto, F. Matsuda, H. Shirahama, Synlett, 1991,202; (b) M. Isobe, T. Nishikawa, N. Yamamoto, T. Tsukiyama, A. Ino, T. Okita, J. Heterocycl. Chem. 1992, 29, 619; (c) J. P. Michael, Nat. Prod. Rep. 1997, 14, 605] and drugs [(a) D. G. Markees, V. C. Dewey, G. W. Kidder, J. Med. Chem. 1970, 13, 324; (b) A. A. Alhaider, M. A. Abdelkader, E. J. Lien, J. Med. Chem. 1985, 28,1398; (c) S. F. Campbell, J. D. Hardstone, M. J. Palmer, J. Med. Chem. 1988, 31,1031]. Several quinoline derivatives have been found to possess useful biological activities like antibacterial (H. V. Patel, K. V. Vyas, P. S. Fernandes; Indian J. Chem. 1990, 29B, 836.), antimalarial, anti-inflammatory etc. Thus quinoline heterocyclic ring system occupies a pride of place in organic and medicinal chemistry by way of useful biological profiles as mentioned above. Skraup's (H. Skraup, Chem. Ber. 1880, 13, 2086; R. H. F. Mansake, M. Kulka, Org.React. 1953,7,59.) procedure is the classical method for the construction of quinoline nucleus requiring drastic reaction conditions using sulfuric acid as catalyst. Many methods have been reported for the synthesis of quinolines and most of them suffer from drawbacks like use of hazardous and expensive reagents, drastic reaction conditions and poor yields. In another approach quinoline skeleton is prepared by the reaction of aminoarenes and olefins employing transition metal complexes as catalysts [(a) S. E. Diamond, A. Szalkiewicz, F. Mares, J. Am. Chem. Soc. 1979,101, 490; (b) T. Joh, N. Hagihara, Tetrahedron Lett. 1967, 8, 4199). The quinoline moiety can also be prepared by the reaction of aminoarenes with aliphatic aldehydes under non acidic conditions (Y. Watanabe, S. C. Shim, T. Mitsudo, Bull. Chem. Soc. Jpn.1981, 54, 3460).

Reference may be made to F. N. Campbell, I. J. Scchaffner, J. A. C. S., 1995, 67, 86-89; M. A. Clapp, R. S. Yipson, J. A. C. S., 1946, 68,1332-34; J. Spencer, M. Pfeffer, Tetrahedron Asymmetry, 1995, 6(2),419-426.

All the existing methods for the preparation of quinoline ring skeleton have the following disadvantages.

1. Use of hazardous chemicals like concentrated sulfuric acid, which is corrosive and produce waste at the source, requiring effluent treatment, and have negative influence on the economy.
2. It is inconvenient to handle concentrated sulfuric acid in large-scale synthesis.
3. Drastic reaction conditions i.e. carrying out the reaction at high temperatures.
4. Use of expensive transition metal complexes thereby polluting the environment.
5. Purification of the product using column chromatography or preparative thin layer chromatography is not economical on large-scale process, since the yield of the product will be reduced.
6. Significant yield variations with variant substituents on phenyl ring.

OBJECTIVES OF THE INVENTION

The main objective of the present invention is to provide an improved process for the synthesis of quinoline derivatives, which obviates the above drawbacks.

Another object is to provide an improved process for the synthesis of quinoline derivatives by using two catalysts.

SUMMARY OF THE INVENTION

Accordingly the present invention provides an improved process for the synthesis of quinoline derivatives

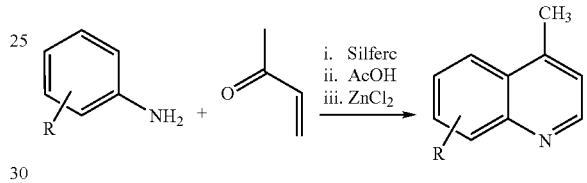

wherein R=alkyl, aryl, alkyloxy, halo, nitro or amino group which comprises stirring the solution of aniline or substituted aniline in acetic acid, in the presence of a catalyst 'silferc' with a molar ratio of substituted aniline to catalyst in the range of 1:1 to 1:3, under inert atmosphere, for a period of 3-6 minutes, adding methyl vinyl ketone slowly on the above said reaction mixture over a period of 10-30 minutes, followed by heating to a temperature in the range of 50-90° C., for about 1 hr, further adding a second catalyst 'anhydrous zinc chloride' to the above said reaction mixture and refluxing it for a period of 2-5 hrs, cooling, filtering and basifying the above said resultant reaction mixture with 5-10% NaOH solution, followed by extraction with ethyl acetate, drying and evaporating the resultant extract to obtain the desired product in pure form.

In an embodiment of the present invention the group 'R' used in substituted aniline is selected from the group consisting of alkyl, aryl, alkyloxy, halo, nitro or amino group.

In yet another embodiment the silferc catalyst used is an anhydrous ferric chloride impregnated silica gel.

In yet another embodiment the molar ratio of substituted aniline to 'silferc' catalyst used is in the range of 1:1 to 1:1.5.

In yet another embodiment the inert atmosphere used is nitrogen environment.

In yet another embodiment the molar ratio of substituted aniline to second catalyst 'zinc chloride' used is in the range of 1:1 to 1:1.5.

In yet another embodiment the temperature used for heating the reaction mixture is in the range of 70-75° C.

In yet another embodiment the quinoline derivative obtained is represented by a group of the following compounds:

4-methylquinoline, 8-methoxy-4-methylquinoline, 6-methoxy-4-methyl quinoline, 4,8-dimethylquinoline, 4,6-dimethylquinoline, 8-ethyl-4-methylquinoline, 8-chloro-4-

Methylquinoline, 8-fluoro-4-methylquinoline, 6-hydroxy-4-methylquinoline, and nitro-4-methylquinoline.

In still another embodiment the yield of quinoline derivative obtained is in the range of 55-65%

Novelty of the present invention lies in the use of two separate catalyst, particularly the 'silferc' catalyst in the synthesis of quinoline derivatives, thereby avoiding volatile organic solvent used in conventional methods, thus offers clean and green chemical approach. The % yield of the product in the present invention is higher than the one reported in conventional methods.

DETAIL DESCRIPTION OF THE INVENTION

Keeping in demand for the synthesis of this important heterocycle, herein we report a simple one-pot process for the preparation of quinoline and its derivatives from readily available anilines and methyl vinyl ketone (MVK) in the presence of twin catalysts. The catalyst silferc is prepared by impregnating anhydrous ferric chloride on silica gel in appropriate amounts by co-grinding technique in an agate mortar and activated at 50-90° C. for 3-6 hours to obtain light brown free flowing powder.

In a typical procedure aniline (1 molar eq.), silferc (ferric chloride content 1-3 molar eq.) in acetic acid are heated to 50-70° C. Methyl vinyl ketone (MVK) (1.2-2.0 molar eq.) was added over a period of 10-30 minutes and refluxed. After 1-2 hours of reflux, anhydrous zinc chloride (1-2 molar eq.) was added and the reaction was further refluxed for 2-5 hours. The reaction mixture was cooled, filtered, basified with 5-10% NaOH solution, extracted with ethyl acetate, dried over $Na_2SO_4$ and evaporated to give the product in pure form.

The following examples are given by the way of illustration and therefore should not be construed to limit the scope of the invention. These examples should not be construed as limiting.

In the drawing, FIG. 1 represents the preparation of quinoline derivatives.

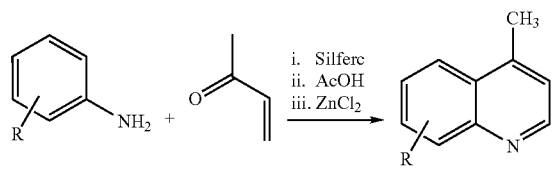

EXAMPLE 1

Preparation of 4-Methylquinoline

To a stirred solution of aniline (1 g. 10 mmol) in acetic acid (10 ml), activated silferc (1.72 g. ferric chloride 10 mmol) was added under nitrogen atmosphere. The reaction mixture was stirred for 5 minutes and methyl vinyl ketone (MVK) (0.83 g, 11.8 mmol) was added slowly over a period of 15 minutes. The reaction mixture was heated to 70° C. and maintained between 70-75° C. for one hour. Anhydrous zinc chloride (1.46 g. 10 mmol) was added and the reaction was further refluxed for two hours. The reaction mixture was cooled, filtered, basified with 10% NaOH solution, extracted with ethyl acetate (3×20 ml), dried over $Na_2SO_4$ and evaporated to give the product; Yield 55%.

EXAMPLE 2

Preparation of 8-Methoxy-4-Methylquinoline

To a stirred solution of 2-methoxyaniline (1 g. 8.1 mmol.) in acetic acid (10 ml), activated silferc (1.3 g. ferric chloride 8.1 mmol) was added under nitrogen atmosphere. The reaction mixture was stirred for 5 minutes and methyl vinyl ketone (MVK) (0.62 g, 8.9 mmol) was added slowly over a period of 15 minutes. The reaction mixture was heated to 70° C. and maintained between 70-75° C. for one hour. Anhydrous zinc chloride (1.1 g. 8.1 mmol) was added and the reaction was further refluxed for two hours. The reaction mixture was cooled, filtered, basified with 10% NaOH solution, extracted with ethyl acetate (3×20 ml), dried over $Na_2SO_4$ and evaporated to give the product; Yield 60%.

EXAMPLE 3

Preparation of 6-Methoxy-4-Methylquinoline

To a stirred solution of 4-methoxyaniline (1 g. 8.1 mmol.) in acetic acid (10 ml), activated silferc (1.3 g., ferric chloride 8.1 mmol) was added under nitrogen atmosphere. The reaction mixture was stirred for 5 minutes and methyl vinyl ketone (MVK) (0.62 g, 8.9 mmol) was added slowly over a period of 15 minutes. The reaction mixture was heated to 70° C. and maintained between 70-75° C. for one hour. Anhydrous zinc chloride (1.1 g. 8.1 mmol) was added and the reaction was further refluxed for two hours. The reaction mixture was cooled, filtered, basified with 10% NaOH solution, extracted with ethyl acetate (3×20 ml), dried over $Na_2SO_4$ and evaporated to give the product; Yield 58%.

EXAMPLE 4

Preparation of 4,8-Dimethylquinoline

To a stirred solution of 2-methylaniline (1 g. 9.3 mmol.) in acetic acid (10 ml), activated silferc (1.5 g., ferric chloride 9.3 mmol) was added under nitrogen atmosphere. The reaction mixture was stirred for 5 minutes and methyl vinyl ketone (MVK) (0.72 g, 10.2 mmol) was added slowly over a period of 15 minutes. The reaction mixture was heated to 70° C. and maintained between 70-75° C. for one hour. Anhydrous zinc chloride (1.27 g. 9.3 mmol) was added and the reaction was further refluxed for two hours. The reaction mixture was cooled, filtered, basified with 10% NaOH solution, extracted with ethyl acetate (3×20 ml), dried over $Na_2SO_4$ and evaporated to give the product; Yield 65%.

EXAMPLE 5

Preparation of 4,6-Dimethylquinoline

To a stirred solution of 4-methylaniline (1 g. 9.3 mmol.) in acetic acid (10 ml), activated silferc (1.5 g. ferric chloride 9.3 mmol) was added under nitrogen atmosphere. The reaction mixture was stirred for 5 minutes and methyl vinyl ketone (MVK) (0.72 g, 10 mmol) was added slowly over a period of 15 minutes. The reaction mixture was heated to 70° C. and maintained between 70-75° C. for one hour. Anhydrous zinc chloride (1.27 g. 9.3 mmol) was added and the reaction was further refluxed for two hours. The reaction mixture was cooled, filtered, basified with 10% NaOH solution, extracted with ethyl acetate (3×20 ml), dried over Na$_2$SO$_4$ and evaporated to give the product; Yield 60%.

EXAMPLE 6

Preparation of 8-Ethyl-4-Methylquinoline

To a stirred solution of 2-ethylaniline (1 g. 8.2 mmol.) in acetic acid (10 ml), activated silferc (1.32 g. ferric chloride 8.2 mmol) was added under nitrogen atmosphere. The reaction mixture was stirred for 5 minutes and methyl vinyl ketone (MVK) (0.63 g, 9 mmol) was added slowly over a period of 15 minutes. The reaction mixture was heated to 70° C. and maintained between 70-75° C. for one hour. Anhydrous zinc chloride (1.12 g. 8.2 mmol) was added and the reaction was further refluxed for two hours. The reaction mixture was cooled, filtered, basified with 10% NaOH solution, extracted with ethyl acetate (3×20 ml), dried over Na$_2$SO$_4$ and evaporated to give the product; Yield 60%.

EXAMPLE 7

Preparation of 8-Chloro-4-Methylquinoline

To a stirred solution of 2-chloroaniline (1 g. 7.8 mmol.) in acetic acid (10 ml), activated silferc (1.25 g. ferric chloride 7.8 mmol) was added under nitrogen atmosphere. The reaction mixture was stirred for 5 minutes and methyl vinyl ketone (MVK) (0.6 g, 8.5 mmol) was added slowly over a period of 15 minutes. The reaction mixture was heated to 70° C. and maintained between 70-75° C. for one hour. Anhydrous zinc chloride (1.0 g. 7.8 mmol) was added and the reaction was further refluxed for two hours. The reaction mixture was cooled, filtered, basified with 10% NaOH solution, extracted with ethyl acetate (3×20 ml), dried over Na$_2$SO$_4$ and evaporated to give the product; Yield 62%.

EXAMPLE 8

Preparation of 8-Fluoro-4-Methylquinoline

To a stirred solution of 2-fluoroaniline (1 g. 9.0 mmol.) in acetic acid (10 ml), activated silferc (1.4 g. ferric chloride 9.0 mmol) was added under nitrogen atmosphere. The reaction mixture was stirred for 5 minutes and methyl vinyl ketone (MVK) (0.7 g, 9.9 mmol) was added slowly over a period of 15 minutes. The reaction mixture was heated to 70° C. and maintained between 70-75° C. for one hour. Anhydrous zinc chloride (1.2 g. 9.0 mmol) was added and the reaction was further refluxed for two hours. The reaction mixture was cooled, filtered, basified with 10% NaOH solution, extracted with ethyl acetate (3×20 ml), dried over Na$_2$SO$_4$ and evaporated to give the product; Yield 65%.

EXAMPLE 9

Preparation of 6-Hydroxy-4-Methylquinoline

To a stirred solution of 4-hydroxyaniline (1 g. 9.1 mmol.) in acetic acid (10 ml), activated silferc (1.46 g. ferric chloride 9.1 mmol) was added under nitrogen atmosphere. The reaction mixture was stirred for 5 minutes and methyl vinyl ketone (MVK) (0.70 g, 10.1 mmol) was added slowly over a period of 15 minutes. The reaction mixture was heated to 70° C. and maintained between 70-75° C. for one hour. Anhydrous zinc chloride (1.24 g. 9.1 mmol) was added and the reaction was further refluxed for two hours. The reaction mixture was cooled, filtered, basified with 10% NaOH solution, extracted with ethyl acetate (3×20 ml), dried over Na$_2$SO$_4$ and evaporated to give the product; Yield 65%.

EXAMPLE 10

Preparation of 5-Nitro-4-Methylquinoline

To a stirred solution of 3-nitroaniline (1 g. 7.2 mmol.) in acetic acid (10 ml), activated silferc (1.15 g. ferric chloride 7.2 mmol) was added under nitrogen atmosphere. The reaction mixture was stirred for 5 minutes and methyl vinyl ketone (MVK) (0.55 g, 7.9 mmol) was added slowly over a period of 15 minutes. The reaction mixture was heated to 70° C. and maintained between 70-75° C. for one hour. Anhydrous zinc chloride (1.0 g. 7.2 mmol) was added and the reaction was further refluxed for two hours. The reaction mixture was cooled, filtered, basified with 10% NaOH solution, extracted with ethyl acetate (3×20 ml), dried over Na$_2$SO$_4$ and evaporated to give the product; Yield 64%.

The significant advantages of the present invention are:
1. Use of 'silferc' catalyst in the synthesis of quinoline derivatives avoids volatile organic solvent used in conventional methods, thereby offers clean and green chemical approach.
2. This process has general applicability with variety of substituents on the phenyl ring.
3. The present invention provides relatively high yield of 55-65% as compare to 28-45% in the conventional methods.
4. The process is a one pot process

What is claimed is:
1. A process for the synthesis of quinoline derivatives

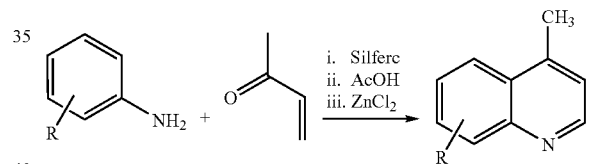

wherein R=H, OH, alkyl, aryl, alkyloxy, halo or nitro group which comprises stirring the solution of aniline or substituted aniline in acetic acid, in the presence of a catalyst 'silferc' with a molar ratio of substituted aniline to catalyst in the range of 1:1 to 1:3, under inert atmosphere, for a period of 3-6 minutes, adding methyl vinyl ketone slowly to the above reaction mixture over a period of 10-30 minutes, followed by heating to a temperature in the range of 50-90° C., for about 1 hr, further adding a second catalyst 'anhydrous zinc chloride' to the above said reaction mixture and refluxing it for a period of 2-5 hrs, cooling, filtering and basifying the above resultant reaction mixture with 5-10% NaOH solution, followed by extraction with ethyl acetate, drying and evaporating the resultant extract to obtain the quinoline derivative in pure form.

2. The process as claimed in claim 1, wherein the group R used in substituted aniline is selected from the group consisting of alkyl, aryl, alkyloxy, halo and nitro group.

3. The process as claimed in claim 1, wherein the silferc catalyst used is an anhydrous ferric chloride impregnated silica gel.

4. The process as claimed in claim 1, wherein the molar ratio of substituted aniline to 'silferc' catalyst used is in the range of 1:1 to 1:1.5.

5. The process as claimed in claim 1, wherein the inert atmosphere used is nitrogen environment.

6. The process as claimed in claim 1, wherein the molar ratio of substituted aniline to second catalyst 'zinc chloride' used is in the range of 1:1 to 1:1.5.

7. The process as claimed in claim 1, wherein the temperature used for heating the reaction mixture is in the range of 70-75° C.

8. The process as claimed in claim 1, wherein the quinoline derivative obtained is one selected from the group consisting of: 4-methylquinoline, 8methoxy-4-methylquinoline, 6-methoxy-4-methyl quinoline, 4,8-dimethylquinoline, 4,6-dimethylquinoline, 8-ethyl-4-methylquinoline, 8-chloro-4-Methylquinoline, 8-fluoro-4-methylquinoline, 6-hydroxy-4-methylquinoline, and nitro-4-methylquinoline.

9. The improved process as claimed in claim 1, wherein the yield of quinoline derivative obtained is in the range of 55-65%.

10. The process as claimed in claim 1, wherein the group R used in substituted aniline is H group.

11. The process as claimed in claim 1, wherein the group R used in substituted aniline is OH group.

* * * * *